US009600628B2

(12) United States Patent
Kisilev et al.

(10) Patent No.: US 9,600,628 B2
(45) Date of Patent: Mar. 21, 2017

(54) AUTOMATIC GENERATION OF SEMANTIC DESCRIPTION OF VISUAL FINDINGS IN MEDICAL IMAGES

(71) Applicant: International Business Machines Corporation, Armonk, NY (US)

(72) Inventors: Pavel Kisilev, Maalot (IL); Eugene Walach, Haifa (IL); Ella Barkan, Haifa (IL); Sharbell Hashoul, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 157 days.

(21) Appl. No.: 14/277,805

(22) Filed: May 15, 2014

(65) Prior Publication Data

US 2015/0332111 A1    Nov. 19, 2015

(51) Int. Cl.
G06K 9/00    (2006.01)
G06F 19/00   (2011.01)
G06T 7/00    (2017.01)
G06K 9/62    (2006.01)

(52) U.S. Cl.
CPC ......... *G06F 19/321* (2013.01); *G06T 7/0012* (2013.01); *G06K 9/627* (2013.01); *G06K 9/6232* (2013.01)

(58) Field of Classification Search
CPC ................................ G06K 9/46; G06T 7/0012
USPC ................................................. 382/128, 131
See application file for complete search history.

(56) References Cited

U.S. PATENT DOCUMENTS

| 7,756,309 | B2 | 7/2010 | Gholap et al. | |
| 9,111,547 | B2* | 8/2015 | Loui | G10L 25/51 |
| 2005/0105775 | A1* | 5/2005 | Luo | G06F 17/30247 382/115 |
| 2008/0292194 | A1* | 11/2008 | Schmidt | G06T 7/0012 382/217 |
| 2012/0020536 | A1 | 1/2012 | Moehrle | |
| 2014/0046696 | A1* | 2/2014 | Higgins | G06F 19/345 705/3 |

OTHER PUBLICATIONS

Kulkarni et al., "Baby Talk: Understanding and Generating Image Descriptions", IEEE conference on Computer Vision and Pattern Recognition CVPR, Jun. 20-25, 2011, pp. 1601-1608.
Ordonez et al., "Im2Text: Describing Images Using 1 Million Captioned Photographs", Advances in Neural Information Processing Systems 24, 2011, pp. 1143-1151.
Farhadi et al., "Every Picture Tells a Story: Generating Sentences from Images", Computer Vision ECCV 2010, Lecture Notes in Computer Science vol. 6314, 2010, pp. 15-29.
Mechouche et al., "Semantic description of brain MRI images", SWAMM 2006 Workshop, Ireland 2006.
Park et al., "Automatic extraction of semantic concepts in medical images", 2004 International Conference on Image Processing ICIP '04, Oct. 24-27, 2004, pp. 1157-1160, vol. 2.

* cited by examiner

*Primary Examiner* — Tom Y Lu

(57) ABSTRACT

A method comprising using at least one hardware processor for applying a mapping function to a medical image, to generate a semantic description of a visual finding in the medical image. The mapping function is optionally an MRF (Markov random field)-based, SVM (Support Vector Machine) mapping function.

18 Claims, 2 Drawing Sheets

AUTOMATIC GENERATION OF SEMANTIC DESCRIPTION OF VISUAL FINDINGS IN MEDICAL IMAGES

BACKGROUND

As medical image acquisition systems become more prevalent, many healthcare experts, such as radiologists and physicians, face the problem that the time available for the examination of the images decreases. Consequently, there is a growing need for diagnosis support systems to assist in the examination.

For ease of storage and retrieval, medical images are commonly collected in databases which may take many forms, such as local folders on a computer system, accessible to individual users or to multiple users, or the more widespread PACS (Picture Archiving and Communication System). The ability to search the databases and retrieve relevant medical images therefore becomes increasingly important.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising using at least one hardware processor for applying a mapping function to a medical image, to generate a semantic description of a visual finding in the medical image.

There is further provided, in accordance with an embodiment, a method comprising using at least one hardware processor for: providing, to one or more medical experts, a training set comprising multiple medical images; receiving, from the one or more medical experts, semantic descriptions of visual findings in the multiple medical images; and training an SVM (Support Vector Machine) algorithm based on the training set and on an MRF (Markov random field) modeling of the semantic descriptions, to produce a mapping function of visual findings to semantic descriptions.

There is yet further provided, in accordance with an embodiment, a computer program product for semantic description of visual findings in medical images, the computer program product comprising a non-transitory computer-readable storage medium having program code embodied therewith, the program code executable by at least one hardware processor to: applying an MRF (Markov random field)-based, SVM (Support Vector Machine) mapping function to a medical image, to generate a semantic description of a visual finding in the medical image.

In some embodiments, the mapping function is an MRF (Markov random field)-based, SVM (Support Vector Machine) mapping function.

In some embodiments, the semantic description comprises a qualitative text.

In some embodiments, the semantic description comprises a quantitative text.

In some embodiments, the semantic description comprises a medical lexicon term.

In some embodiments, the medical lexicon is RadLex.

In some embodiments, the semantic description comprises a name of a parameter and a value of the parameter.

In some embodiments, the visual finding comprises an image feature associated with a portion of the medical image.

In some embodiments, the medical image is selected from the group consisting of: an X-Ray image, an MRI (Magnetic Resonance Imaging) image, a CT (Computerized Tomography) image, an angiography image, an ultrasound image, a nuclear image, a thermographic image and an echocardiographic image.

In some embodiments, the method further comprises using said at least one hardware processor for applying the mapping function to a medical image under investigation, to generate a semantic description of a visual finding in the medical image under investigation In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein is the automatic generation of semantic descriptions of visual findings in medical images. These semantic descriptions, which may bear the form of qualitative and/or quantitative textual tags, may be used to automate the process of medical imagery analysis, medical imagery retrieval, and more.

In some embodiments, the automatic generation of the semantic descriptions is realized using a structured, supervised, machine learning technique. For example, a training set of multiple medical images may be provided to one or more medical experts, such as radiologists and/or the like. Then, these medical experts may visually examine the images, and compose semantic descriptions of various visual findings in these images. These semantic descriptions may then be modeled as a Markov random field (MRF). Finally, an SVM (Support Vector Machine) algorithm may be trained based on the training set and on the MRF model of the semantic descriptions, to produce a mapping function of visual findings to semantic descriptions.

The produced mapping function may be later applied to a medical image under investigation, in order to generate one or more semantic descriptions of one or more visual findings, respectively, in the medical image.

Figure 1:
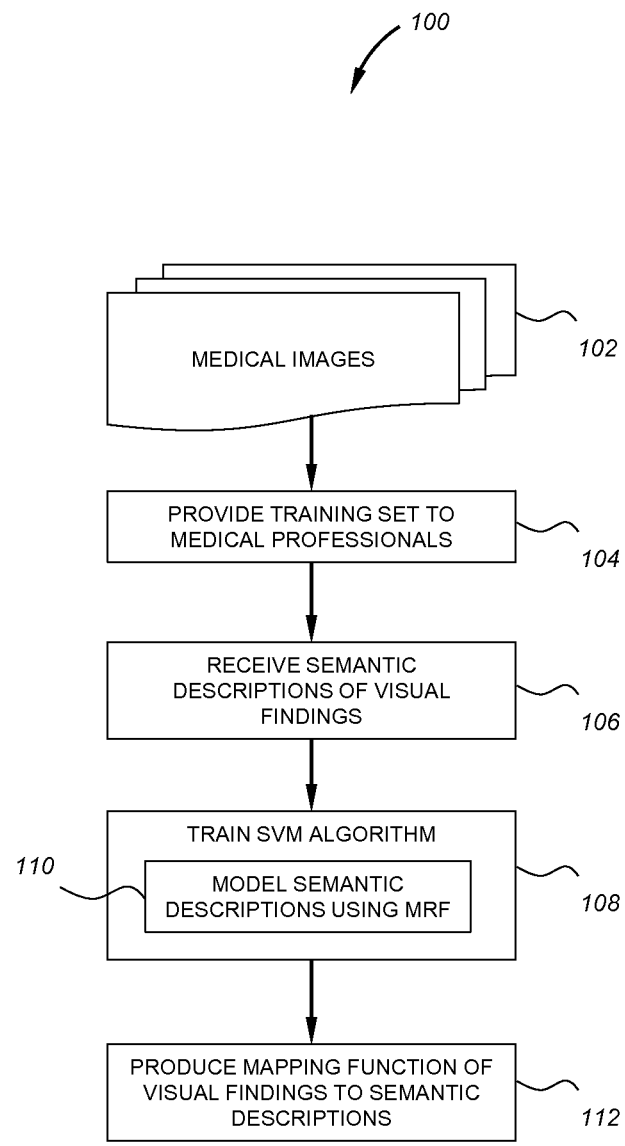
FIG. 1 shows a flow chart of a method for producing a mapping function of visual findings to semantic descriptions.

Reference is now made to FIG. 1, which shows a flow chart of a method 100 for producing a mapping function of visual findings to semantic descriptions, in accordance with an embodiment. In some embodiments, method 100 may be carried out separately for different medical imagery types, to produce different mapping functions, respectively. Namely, each mapping function may map visual findings in a specific medical imagery type to semantic descriptions. Exemplary medical imagery types are discussed below with reference to multiple medical images 102.

In a step 104, a training set which includes multiple medical images 102 may be provided to one or more medical experts. These medical experts may be radiologists and/or any other persons skilled at interpreting medical imagery.

The training set may include one or more descriptors of visual features which are extracted from each of medical images 102 using one or more feature extraction algorithms, as known in the art. The one or more feature extraction algorithms may be applied to the entirety of each image, and/or to one or more regions of interest (ROIs) in each image. The ROIs may be automatically computed, as known in the art, and/or manually indicated by the medical experts to which medical images 102 are provided. For example, a medical expert may draw, on a medical image, the boundary of an ROI.

Medical images 102 may include, for example, one or more of an X-Ray image, an MRI (Magnetic Resonance Imaging) image, a CT (Computerized Tomography) image, an angiography image, an ultrasound image, a nuclear image, a thermographic image, an echocardiographic image and/or any other type of medical image. Medical images 102 may be provided in digital form, namely—as digital image files.

In a step 106, semantic descriptions of visual findings in medical images 102 may be received, as textual input, from the one or more medical experts. The one or more medical experts may compile these semantic descriptions as follows: They may visually examine medical images 102, for example by viewing them on a computer screen. When one of these medical experts makes a visual finding in one of medical images 102, he or she may use a computerized user interface for providing a semantic description of the visual finding. Exemplary visual findings include lesions, tumors, stenosis, etc. Generally, any observable detail in a medical image, which is determined by a medical expert to be of importance, may be defined as a visual finding. In computerized image analysis terminology, a visual finding may be an image feature which spans over a portion of the medical image (which portion may be contiguous or non-contiguous).

The semantic descriptions may be provided in standard medical terminology, as commonly used by radiologists and/or other medical imagery interpreters for describing their visual findings. For example, the semantic descriptions may include medical lexicon terms, such as terms from RadLex, a medical lexicon composed and maintained by the Radiological Society of North America (RSNA), and available at http://radlex.org. Another example of a medical lexicon is the BI-RADS Atlas, composed and maintained by the American College of Radiology (ACR), and available at http://www.acr.org/Quality-Safety/Resources/BIRADS. The BI-RADS Atlas includes standardized breast imaging findings terminology, report organization, assessment structure and a classification system for mammography, ultrasound and MRI (Magnetic Resonance Imaging) of the breast.

The semantic descriptions may include qualitative and/or quantitative texts which characterize the visual findings, in accordance with the standard medical terminology. A quantitative text may be one which provides a numerical value characterizing the finding. For example, if stenosis of a blood vessel is found, the severity of the stenosis may be expressed using a numerical value indicating the percentage of stenosis compared to an original diameter of the vessel. As another example, if a suspicious mass is found, its measurements may be expressed numerically. Such quantitative texts may be the result of a measurement performed by the medical expert, for example using measurement tools in a graphic user interface (GUI), as known in the art.

A qualitative text, on the other hand, may be one which provides the nature of the visual finding, as opposed to a numerical characteristic thereof. For example, in an angiogram showing a blood vessel with a certain narrow segment, the qualitative text may be "stenosis", which is the medical term for this visual finding. As another example, if a suspicious mass is found, its shape and margin type may be expressed by qualitative texts such as "Mass shape: Lobular" and "Mass margin: Spiculated".

It should be emphasized that any one visual finding may be expressed by a combination of one or more qualitative texts and one or more quantitative texts, as suitable for correctly and fully describing that finding. In addition, any one of medical images 102 may include one or multiple visual findings.

The semantic description of a visual finding is optionally structured as name-value pairs. Namely, a semantic description may include a name of a parameter (e.g. "severity", "shape", etc.) and a corresponding value of that parameter (e.g. "90%", "lobular", etc., respectively).

In a step 108, an SVM (Support Vector Machine) algorithm may be trained, based on the training set of medical images 102, and, advantageously, on an MRF (Markov random field) modeling 110 of the semantic descriptions received in step 106. Specifically, the descriptors of visual features extracted earlier may serve as the training set for the SVM algorithm. As an alternative to MRF modeling 110, conditional random field (CRF) modeling, as known in the art, may be used.

Figure 2:
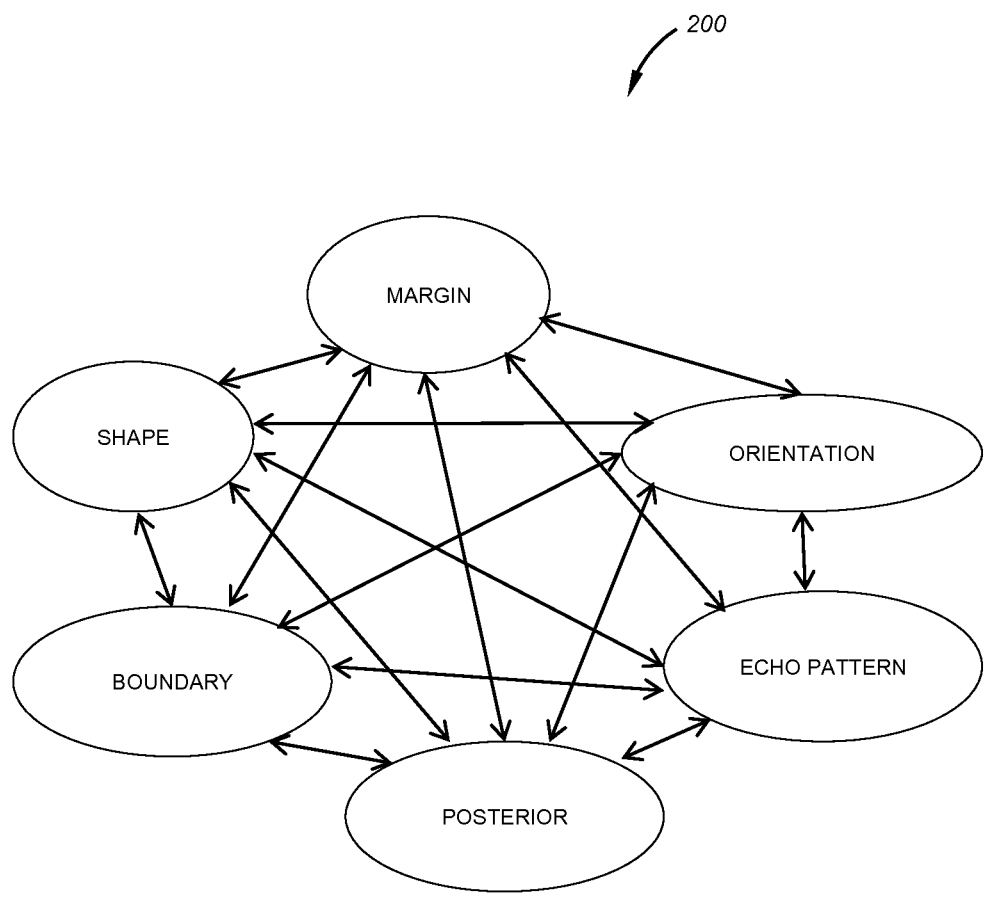
FIG. 2 shows a diagram of semantic descriptions modeled as a Markov random field (MRF).

MRF modeling 110 may include an analysis of the semantic descriptions, to detect dependencies between different semantic descriptions. Interim reference is now made to FIG. 2, which shows an exemplary MRF model 200 of semantic descriptions of mammography, ultrasound and MRI images of the breast, in accordance with the BI-RADS Atlas.

The training of the SVM algorithm may include, initially, a structured definition of a learning problem. Advantageously, the learning problem may be posed as a search for an optimal set of weights w of the linear combination of feature functions, so that the ground truth multi-label vector score is higher than all other possible combinations of labels:

$$u = \underset{u, \xi \geq 0}{\arg\min} \frac{1}{2}\|u\|^2 + C\xi$$

$$s.t. \frac{1}{N}\sum_{i=1}^{N} \max_{\bar{y}_i \in Y}[\Delta(y_i, \bar{y}_i) - \langle u, \psi(I_i, \bar{y}_i)\rangle + \langle u, \psi(I_i, y_i)\rangle] \leq \xi$$

where the various letters and symbols of these formulae are defined in the Example and Experimental Results section below.

The ground truth multi-label vector score may be computed as a Hamming distance, as known in the art, between the semantic descriptions.

Then, the SVM algorithm may be executed in order to solve that learning problem. This execution may produce, in a step 112, a mapping function of visual findings to semantic descriptions:

$$\underset{Y}{\operatorname{argmax}} \hat{w}^T \psi(x, Y)$$

in which $\hat{w}$ is the learned optimal set of weights.

The mapping function, due its method of production, may also be referred to as an MRF-based, SVM mapping function.

The mapping function may be later used in order to automatically generate one or more semantic descriptions of one or more visual findings in a medical image under examination. To this end, the mapping function may be applied to a medical image provided digitally, i.e. as a digital image file. The mapping function may map visual findings in the medical image, as these visual findings are expressed in one or more visual feature descriptors, to one or more suitable semantic descriptions. Prior to this mapping, visual features may be extracted from the medical image, using one or more feature extraction algorithms, as known in the art. This extraction may yield the one or more visual feature descriptors. The one or more feature extraction algorithms may be applied to the entirety of the medical image, and/or to one or more regions of interest (ROIs) in the medical image. The ROIs may be automatically computed, as known in the art, and/or manually indicated by a medical expert.

The one or more semantic descriptions resulting from the application the mapping function to the medical image may be stored in association with the medical image. For example, these semantic descriptions may be stored as meta data inside the digital image file itself, such as in the case a DICOM (Digital Imaging and Communications in Medicine) file format is chosen for storing the medical image. As another example, these semantic descriptions may be saved in a data base, along with a unique identified of the pertinent medical image.

When a large number of medical images are processed by application of the mapping function thereto, the result may be a comprehensive collection of medical images and their associated semantic descriptions. An example of a suitable state-of-the-art system for storing, maintaining and handling such a collection is PACS (Picture Archiving And Communication System). This collection may be queried by an interested user, using methods which are known in the art for tag-based image retrieval.

Advantageously, the mapping function may fully automate the task of medical imagery interpretation, which is commonly a manual process performed by radiologists or the like. Once a medical image is recorded and stored in a computerized system of a healthcare institution (e.g. a PACS system), the mapping function may be automatically applied to the medical image, to generate suitable one or more semantic descriptions and store them. In an alternative implementation, a human expert, such as a radiologist, may be presented with the automatically-generated one or more semantic descriptions and be requested to confirm that they are correct and to make any necessary changes if they are not. While this certainly creates a bottleneck in the interpretation process, it may still be preferred, in some scenarios, as a tradeoff between fully automatic interpretation and fully manual interpretation. In addition, any corrections made by the human expert may be used to enhance the mapping function, by re-training the SVM algorithm based on the corrections.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXAMPLE AND EXPERIMENTAL RESULTS

Given a region of interest (ROI), the following characteristics are typically examined by radiologists. Following the standard radiology lexicon, for sonography images the semantic descriptors are: 1) shape, 2) margin, 3) orientation, 4) acoustic transmission (posterior enhancement/shadowing), 5) lesion boundaries, and 6) echo pattern. Illustration of these semantic descriptors is given in FIG. 2, top. For mammography, the semantic descriptors are: 1) shape, 2) margin, and 3) density. The above characteristics are complex semantic descriptors. The inventors built a diverse set of image measurements related to the above semantic descriptors, and described each one of them quantitatively. These measurements were used in calculation of informative features used in the CRF model. Below are described main discrete values (in parentheses) of the above semantic descriptors, and it is explained how various related image measurements are obtained.

Shape and orientation: The shape of the mass is the most important characteristic examined by radiologists. Malignant tumors tend to have more 'irregular' and 'lobular' shapes. To pick this, we calculate different quantities such as the area of the mass, its aspect ratio, and the curvature along the mass boundaries. Additional shape features are calculated by fitting an ellipse to the mass borders. These features are: the ellipse orientation, the ratio between the minor and the major axes, and various distances (L1 norm, the maximal distance, etc.) between the mass border and the ellipse.

Margin and boundary: 'Sharp' margins may indicate a benign tumor and 'smooth' indicate a malignant one. To assess the sharpness of the boundaries we divided the mass into 8 sectors of 45 degrees and calculate some measure of sharpness of the boundary in each sector.

Acoustic transmission: The posterior of the mass is an important characteristic when assessing the risk of malignancy. Strong 'enhancement' and 'edge shadowing' are common in benign masses (such as cysts), while 'posterior shadowing' is common in malignant tumors. In order to assess the level of the posterior enhancement or shadowing, we detected automatically and examined the area below the mass, and calculated ratios of the median intensities and intensity variances inside its different segments.

Echo pattern: Another important characteristic of masses examined by doctors is their echogenicity compared to the fat tissue. High values may indicate malignancy; the 'echogenicity' and mass 'uniformity' are useful for diagnosis of specific types of tumors. In order to quantify these features we use various heuristics to recognize the fat tissue which is located on the upper side of the US images. We then compare the histogram of the lesion interior values to the one of the fat tissue.

Additional measurements: intensity and texture. To describe texture content of the ROI, we compute local entropy at 3 different scales. We also compute two normalized intensity histograms of the inner and the outer (next to the boundary) areas of the ROI. All the above measurements are combined into the feature vector resulting in 84 continuous values.

Conditional Random Field (CRF) Formulation for Report Generation:

We define the problem of report generation as a learning to map a set of various image measurements to the set of semantic descriptor values. An image finding, or a lesion, is represented by a predefined set of m semantic descriptors that correspond to the nodes of the CRF. The report generated from an image i is an assignment $y_i=[y_{i,1}, \ldots, y_{i,j}]$ where each j-th semantic descriptor $y_{.,j}$ can get one of the possible discrete values $Y_j=\{1, \ldots, V_j\}$ corresponding to the radiological lexicon described above. The CRF energy function of the above assignment for a given image i is a sum of unary and pairwise terms:

$$\sum_{j=1}^{m} u_1^T \Phi_1(y_{ij}, X_i) + \sum_{j,k \in S} u_2^T \Phi_2(y_{ij}, y_{ik}, X_i) + \sum_{j=1}^{m} u_3^T \Phi_3(y_j)$$

where S is the set of all possible pairs of semantic descriptors $\phi_1$, $\phi_2$, and $\phi_3$ are unary, pairwise, and cardinality potentials respectively, defined below. The unary potentials describe the nodes of the CRF; the pairwise potentials describe the edges of the CRF, and capture the likelihood of semantic descriptors to jointly have particular values; cardinality potentials count the number of appearances in the training set of a particular value $Y_j$ for each one of the descriptors divided by corresponding total number of training examples of $Y_j$. The unary potentials are defined as $$\phi_{1,j}(y_{ij}=Y_j, X_i; \theta_{1,j}) \sim P_{Y_j} \doteq Pr(y_{ij}=Y_j|X_i; \theta_{1,j})$$

where $X_i$ is, in general, a set of various image measurements that implicitly related to semantic descriptor values. Further, $\phi_{1,j}$ are the j-th feature model parameters. Intuitively, each channel component can be considered as a predictor of a semantic descriptor $y_{.,j}$ based on a full or partial set of the image measurements $X_i$. The model parameters $\phi_{1,j}$ are learned during the classifiers' training. For that purpose, we used multiclass SVM classifiers whose output scores approximate the above probabilities $P_{Y_j}$. Similarly to the unary potentials, we define the pairwise potentials:

$$\phi_{2,j,k}(y_{ij}=Y_j, y_{ik}=Y_k, X_i; \theta_{2,j}) \sim P_{Y_j,Y_k} \doteq Pr(y_{ij}=Y_j, y_{ik}=Y_k|X_i; \theta_{2,j})$$

However, in this case the number of model parameters and of required training examples are intractable. Therefore, we simplify the model and replace the above probabilities with the normalized number of appearances of corresponding pairs of feature values.

Learning and Inference: Although we formalize the model for report generation in the CRF framework, we learn the model parameters using structured SVM formulation instead of maximum likelihood. Given N training examples, the model parameters $U=[u_1', u_2', u_3']$ in (1) are learned by optimizing the regularized large-margin objective:

$$u = \arg\min_{u, \xi \geq 0} \frac{1}{2}\|u\|^2 + C\xi$$

$$s.t. \frac{1}{N} \sum_{i=1}^{N} \max_{\bar{y}_i \in Y} [\Delta(y_i, \bar{y}_i) - \langle u, \psi(I_i, \bar{y}_i)\rangle + \langle u, \psi(I_i, y_i)\rangle] \leq \xi$$

where for a report with m semantic descriptors the contribution of the potentials is pooled across all nodes and edges, $$\psi(\bar{y}_i, X_i) = \begin{bmatrix} \sum_{j=1}^{m} \phi_1(\bar{y}_{ij}, X_{ij}) \\ \sum_{j,k \in S} \phi_2(\bar{y}_{ij}, \bar{y}_{ik}) \\ \sum_{j=1}^{m} \phi_3(\bar{y}_{ij}) \end{bmatrix}.$$

Our task loss $$\Delta(y_i, \bar{y}_i) = \sum_{j=1}^{m} w_j(y_j \neq \bar{y}_j) \Big/ \sum_{j=1}^{m} w_j$$

is calculated as a normalized weighted Hamming loss with the weights $w_j$ defined (or learned in advance) by the relative importance of descriptors $y_j$ in the diagnosis process. Given the model parameters learned as described above, the inference goal is, for a new image, to find the best assignment whose semantic values result in the lowest task loss. This is achieved by solving $$\hat{y}_i = \arg\min_{\bar{y}_i \in \mathcal{Y}} \langle u, \psi(\bar{y}_i, X_i)\rangle.$$

We obtain the approximate solution of the above problem by using a message-passing algorithm proposed in D. Tarlow, R. P. Adams, and R. S. Zemel. "Randomized optimum models for structured prediction". In Fifteenth International Conference on Artificial Intelligence and Statistics (AIST-ATS), 2012.

After semantic descriptor values are estimated (and a report is generated), the semantic descriptors can be used for the diagnosis decision. The semantic descriptors are features in a standard binary (malignant/benign) or multiclass (specific disease) classification problem. This classification can be performed by any known classification method (for example, SVM).

We used collections of 408 sonography and of 203 mammography images; they contain nearly equal number of benign and malignant cases. Each image is accompanied with a confirmed diagnosis, BI-RADS value, and radiological lexicon descriptor values. For each modality, we performed 10 random subsampling experiments by dividing the whole set of cases into training and testing sets of approximately ⅔ and ⅓ of the overall number of cases, respectively. Both training and testing sets contain equal amount of benign and malignant cases. The ROI where the visual features are calculated from, is obtained by a semi-automatic active contour type lesion boundary detection method. We compared our method with the somewhat competing approaches of (a) F. Narváez, G. Díaz, and E. Romero. "Automatic bi-rads description of mammographic masses". In Digital Mammography, pages 673-681. Springer, 2010, and (b) C.-H. Wei, Y. Li, and P. J. Huang. "Mammogram retrieval through machine learning within bi-rads standards". Journal of biomedical informatics, 44(4):607-614, 2011, which are essentially k-nearest neighbors (KNN) approaches, and of (c) E. Burnside, D. Rubin, and R. Shachter. "A bayesian network for mammography". In Proceedings of the AMIA Symposium, page 106. American Medical Informatics Association, 2000, and (d) D. L. Rubin, E. S. Burnside, and R. Shachter. "A Bayesian network to assist mammography interpretation". In Operations Research and Health Care, pages 695-720. Springer, 2004, which perform each semantic descriptor estimation independently using a classifier. The performance measure we used is the Hamming loss (6) with equal weights, averaged over the testing set of images, and over the 10 random experiments. The results of our experiments are summarized in Table 1. Clearly, our method outperforms the competing approaches. This may be attributed to our more sophisticated model that captures the relationships between different semantic descriptors.

TABLE 1

Comparative results of the semantic descriptors estimation using competing methods. The Hamming loss (6) is used as the quality measure (1 corresponds to perfect prediction).

| Method | Hamming loss (6), sonography set | Hamming loss (6), mammography set |
| --- | --- | --- |
| (a), (b) | 0.58 | 0.52 |
| (c), (d) | 0.65 | 0.61 |
| Ours | 0.71 | 0.64 |

What is claimed is:

1. A method comprising using at least one hardware processor for:
receiving a medical image;
applying a mapping function to the medical image, wherein the mapping function is an SVM (Support Vector Machine) mapping function trained on a training set of medical images using a CRF (Conditional Random Field) model of the relationships between multiple received semantic descriptions of multiple medical findings in the training set;
generating a semantic description of a visual finding in the medical image based on the application of the mapping function; and
storing the medical image in association with the generated semantic description.

2. The method according to claim 1, wherein the semantic description comprises a qualitative text.

3. The method according to claim 1, wherein the semantic description comprises a quantitative text.

4. The method according to claim 1, wherein the semantic description comprises a medical lexicon term.

5. The method according to claim 4, wherein the medical lexicon is RadLex.

6. The method according to claim 1, wherein the semantic description comprises a name of a parameter and a value of the parameter.

7. The method according to claim 1, wherein the visual finding comprises an image feature associated with a portion of the medical image.

8. The method according to claim 1, wherein the medical image is selected from the group consisting of: an X-Ray image, an MRI (Magnetic Resonance Imaging) image, a CT (Computerized Tomography) image, an angiography image, an ultrasound image, a nuclear image, a thermographic image and an echocardiographic image.

9. A method comprising using at least one hardware processor for:
providing, to one or more medical experts, a training set comprising multiple medical images;
receiving, from the one or more medical experts, multiple semantic descriptions of multiple visual findings in the multiple medical images;
training an SVM (Support Vector Machine) algorithm based on the training set and on a CRF (Conditional Random Field) model of the relationships between the multiple semantic descriptions; and
producing a mapping function from the multiple visual findings to the multiple semantic descriptions.

10. The method according to claim 9, wherein the semantic descriptions comprise qualitative texts.

11. The method according to claim 9, wherein the semantic descriptions comprise quantitative texts.

12. The method according to claim 9, wherein the semantic descriptions comprise medical lexicon terms.

13. The method according to claim 12, wherein the medical lexicon is RadLex.

14. The method according to claim 9, wherein the semantic descriptions each comprises a name of a parameter and a value of the parameter.

15. The method according to claim 9, wherein the visual findings each comprises an image feature associated with a portion of one of the multiple medical images.

16. The method according to claim 9, wherein the multiple medical images are each selected from the group consisting of: an X-Ray image, an MRI (Magnetic Resonance Imaging) image, a CT (Computerized Tomography) image, an angiography image, an ultrasound image, a nuclear image, a thermographic image and an echocardiographic image.

17. The method according to claim 9, further comprising using said at least one hardware processor for applying the mapping function to a medical image under investigation, to generate a semantic description of a visual finding in the medical image under investigation.

18. A computer program product for semantic description of visual findings in medical images, the computer program product comprising a non-transitory computer-readable storage medium having program code embodied therewith, the program code executable by at least one hardware processor to:
apply a mapping function to a medical image, wherein the mapping function is an SVM (Support Vector Machine) mapping function trained on a training set of medical images using a CRF (Conditional Random Field) model of multiple relationships between multiple received semantic descriptions of multiple medical findings in the training set;
generate a semantic description of a visual finding in the medical image based on the application of the mapping function; and
store the medical image in association with the generated semantic description.

* * * * *